United States Patent
Takasaki

(10) Patent No.: US 9,492,134 B2
(45) Date of Patent: Nov. 15, 2016

(54) RADIATION IMAGING APPARATUS, AND CONTROL METHOD AND PROGRAM OF THE APPARATUS

(75) Inventor: Takashi Takasaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 401 days.

(21) Appl. No.: 13/522,399

(22) PCT Filed: Jan. 25, 2011

(86) PCT No.: PCT/JP2011/000383
§ 371 (c)(1),
(2), (4) Date: Jul. 16, 2012

(87) PCT Pub. No.: WO2011/093058
PCT Pub. Date: Aug. 4, 2011

(65) Prior Publication Data
US 2012/0288062 A1    Nov. 15, 2012

(30) Foreign Application Priority Data

Jan. 27, 2010   (JP) .................................. 2010-015855

(51) Int. Cl.
*H05G 1/64*    (2006.01)
*A61B 6/00*    (2006.01)

(52) U.S. Cl.
CPC ............. *A61B 6/5205* (2013.01); *A61B 6/542* (2013.01)

(58) Field of Classification Search
CPC ........... G06T 5/50; G06T 2207/10116; A61B 6/482; G01N 23/083
USPC .............................. 378/98.9, 5, 98.11, 98.12
See application file for complete search history.

(56) References Cited

U.S. PATENT DOCUMENTS

| | | | | |
|---|---|---|---|---|
| 3,894,181 A | * | 7/1975 | Mistretta | H04N 5/3205 348/E5.089 |
| 4,029,963 A | * | 6/1977 | Alvarez | A61B 6/032 250/360.1 |
| 4,813,061 A | * | 3/1989 | Kakegawa | H05G 1/60 250/583 |
| 6,925,144 B2 | * | 8/2005 | Matsumoto | A61B 6/032 378/22 |
| 7,274,771 B2 | * | 9/2007 | Allred | A61B 6/032 378/108 |
| 2002/0085671 A1 | * | 7/2002 | Sakaida | A61B 6/4241 378/98.11 |
| 2003/0169850 A1 | * | 9/2003 | Kump | A61B 6/405 378/207 |
| 2004/0102688 A1 | | 5/2004 | Walker et al. | |

(Continued)

FOREIGN PATENT DOCUMENTS

| | | |
|---|---|---|
| JP | 63014984 A | 1/1988 |
| JP | S63-014984 B | 4/1988 |
| JP | 9289985 A | 11/1997 |
| JP | 2773358 B2 | 7/1998 |
| JP | 200069369 A | 3/2000 |

(Continued)

*Primary Examiner* — Michael Maskell
(74) *Attorney, Agent, or Firm* — Canon USA, Inc., IP Division

(57) ABSTRACT

An energy control unit continuously adjusts energy of radiations in one shot emitted by an X-ray irradiation unit. An X-ray detection unit generates a plurality of image data pieces in one shot by detecting the radiations whose energy is continuously adjusted and transmitted through a subject. An image classification unit classifies the plurality of image data pieces generated by the X-ray detection unit into image data generated by the radiations of a high energy side and image data generated by the radiations of a low energy side. An image subtraction unit performs weighting and subtraction on the image data generated by the radiations of the high energy side and the image data generated by the radiations of the low energy side.

35 Claims, 8 Drawing Sheets

(56) References Cited

U.S. PATENT DOCUMENTS

2009/0060312 A1* 3/2009 Kitamura .................. G06T 5/50
382/132
2014/0211909 A1* 7/2014 Yamazaki .............. A61B 6/032
378/4

FOREIGN PATENT DOCUMENTS

| | | |
|---|---|---|
| JP | 2007222311 A | 9/2007 |
| JP | 2009240420 A | 10/2009 |
| JP | 4401751 B2 | 1/2010 |
| WO | 2008072175 A1 | 6/2008 |

* cited by examiner

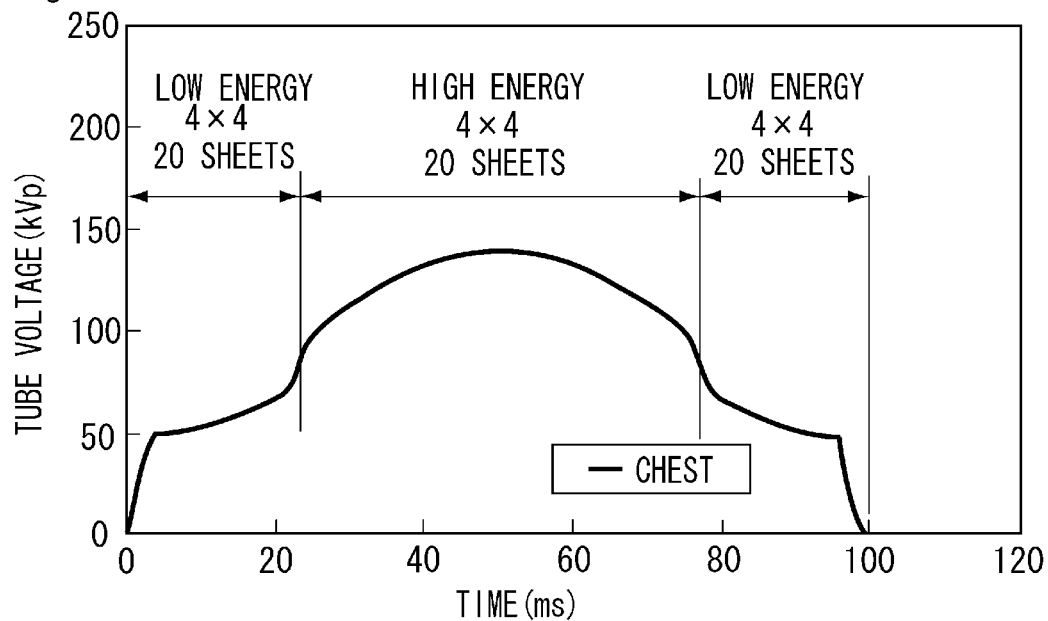
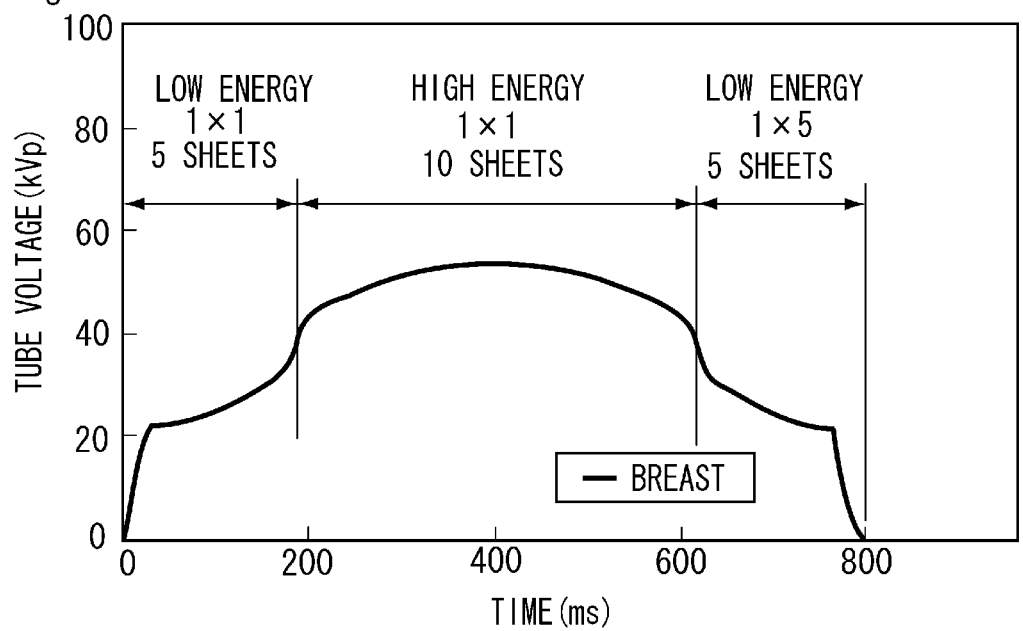

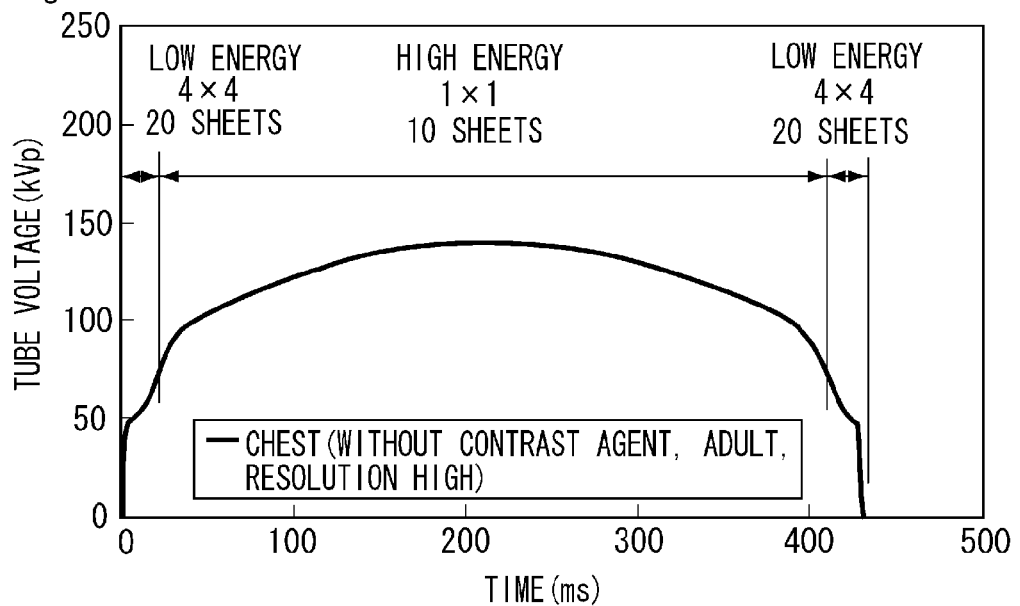

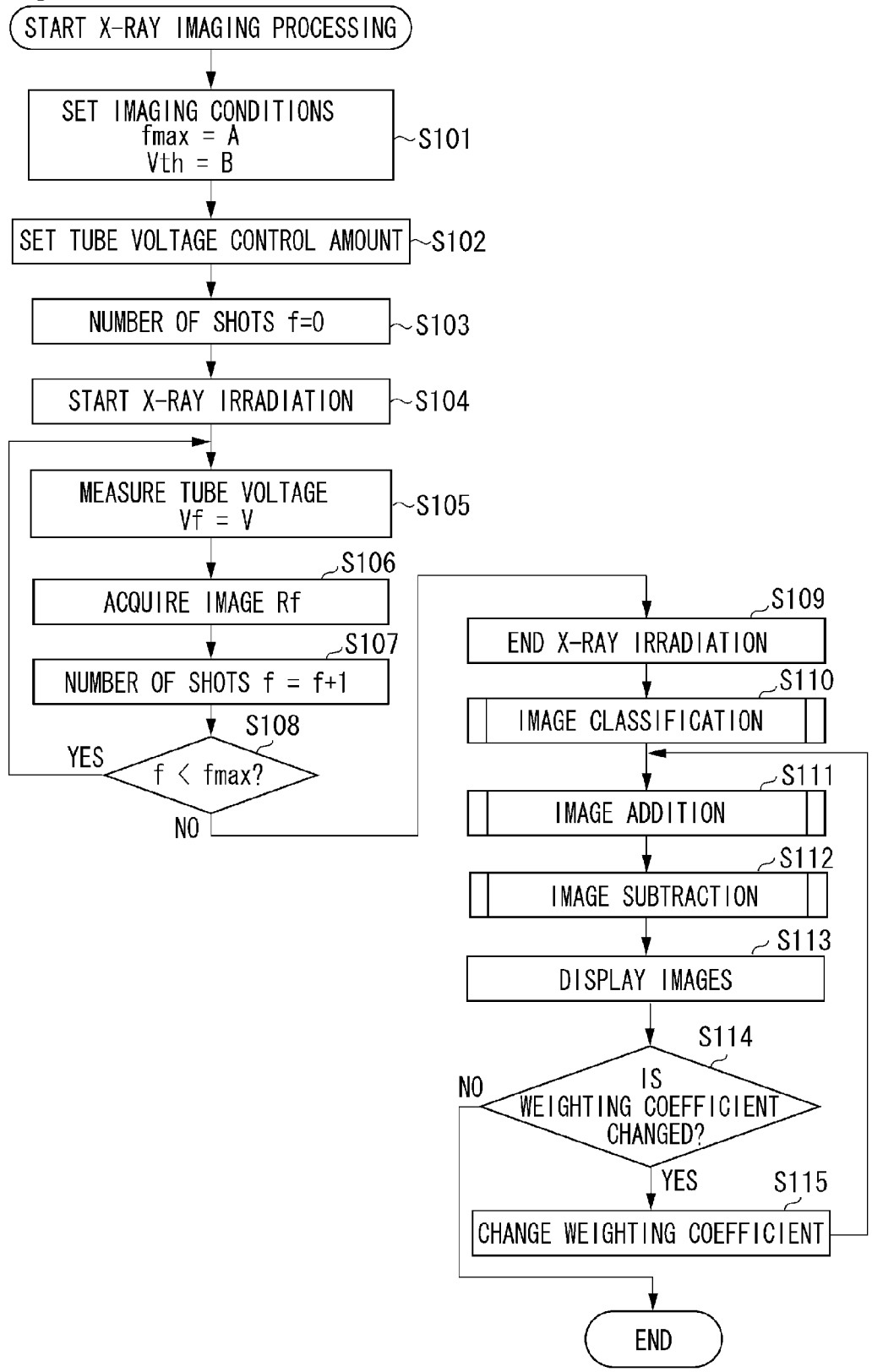

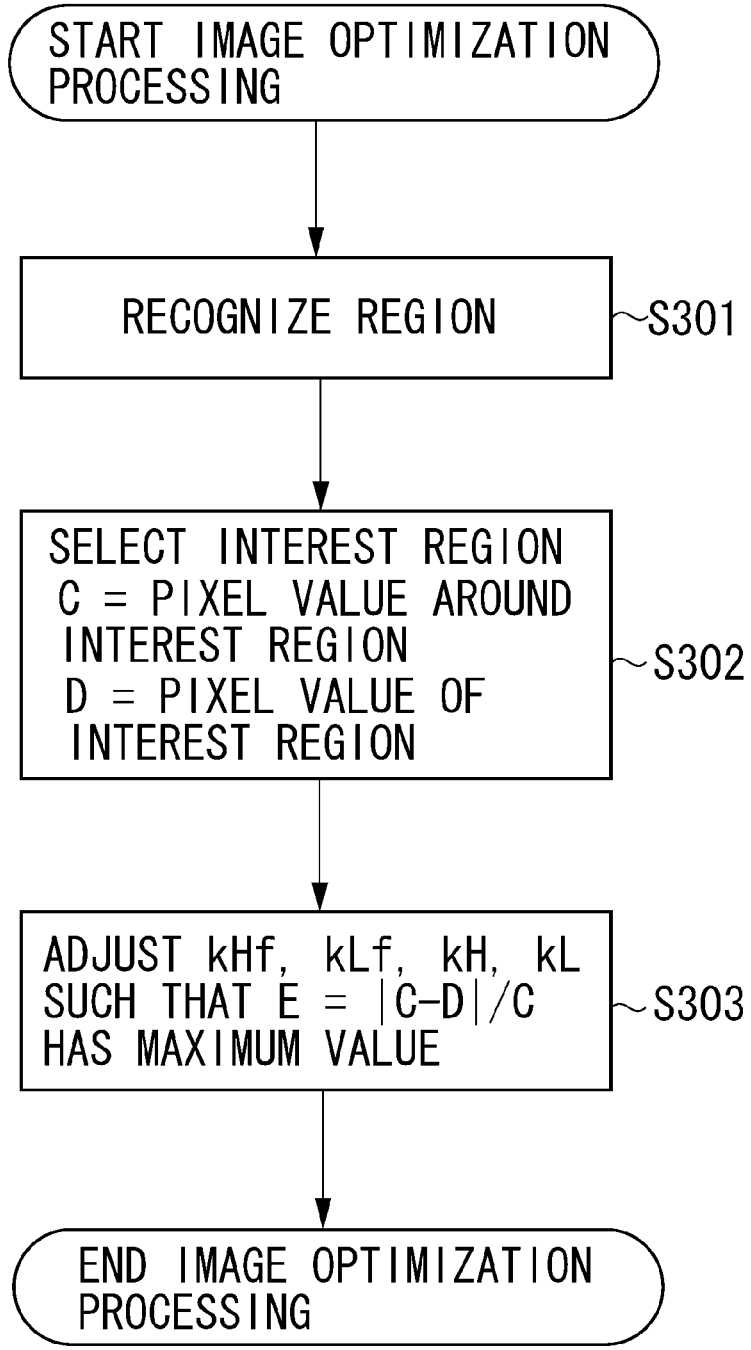

RADIATION IMAGING APPARATUS, AND CONTROL METHOD AND PROGRAM OF THE APPARATUS

TECHNICAL FIELD

The present invention relates to a technique for shooting an image of a subject using radiation.

BACKGROUND ART

An energy subtraction method is an image shooting method for improving visualization of an interest region using a difference of X-ray absorption characteristics of a material depending on energy of the X-rays. More specifically, in the method, a subject is irradiated with X-ray beams having high energy and X-ray beams having low energy, the respective X-ray beams transmitted through the subject are captured as X-ray image data by an image detection unit, and energy subtraction image data is generated by subtracting both of the X-ray image data pieces.

Further, the interest region can be changed by changing a weight to the X-ray image data captured by the high-energy X-ray beams and a weight to the X-ray image data captured by the low-energy X-ray beams. By the change, energy subtraction image data in which tissue of bone portions is erased and soft tissue is extracted as an interest region, and in an opposite manner, energy subtraction image data in which the soft tissue is erased and the bone portion is extracted as the interest region can be obtained.

In the generation of the energy subtraction image data, if each of the energy of the high-energy X-ray beam and the low-energy X-ray beam is not appropriate, the interest region cannot be appropriately extracted. Thus, various methods have been discussed to solve the problem.

In Japanese Patent Application Laid-Open No. 2007-222311, at least in image shooting using the high energy X-ray beam, the energy is discretely changed at a plurality of steps, and X-ray image data is captured at each step. Then, subtraction processing is performed using at least two or more combinations of the X-ray image data captured by the high-energy X-ray beam and the X-ray image data captured by the low-energy X-ray beam, respectively. By this processing, as compared to a case in which only one shot of the X-ray image data captured by the high-energy X-ray beam and one shot of the X-ray image data captured by the low-energy X-ray beam are captured, the possibility of obtaining energy subtraction image data captured with appropriate energy is increased.

However, when the X-ray image data is captured by discretely changing the energy, if there is appropriate energy other than the discrete energy, it is not possible to obtain appropriate energy subtraction image data. Accordingly, in the case of the technique discussed in Japanese Patent Application Laid-Open No. 2007-222311, energy subtraction image data captured with appropriate energy may not be obtained in a single shooting.

CITATION LIST

Patent Literature

PTL 1: Japanese Patent Application Laid-Open No. 2007-222311

SUMMARY OF INVENTION

Solution to Problem

The present invention is directed to obtaining a plurality of pieces of energy subtraction image data in a single shooting.

According to an aspect of the present invention, a radiation imaging apparatus includes an irradiation unit configured to irradiate a subject with radiations, a control unit configured to continuously adjust energy of the radiations in one shot emitted by the irradiation unit, a generation unit configured to generate a plurality of image data pieces in one shot by detecting the radiations whose energy is continuously adjusted by the control unit and transmitted through the subject, a classification unit configured to classify the plurality of image data pieces generated by the generation unit into image data generated by the radiations of a high energy side and image data generated by the radiations of a low energy side, and a subtraction unit configured to perform weighting and subtraction on the image data generated by the radiations of the high energy side and the image data generated by the radiations of the low energy side.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

FIG. 2A illustrates time change in X-ray energy in one shot of the X-rays from an X-ray irradiation unit with which a subject is irradiated and the number of shots of X-ray image data to be captured by one shot of the X-rays.

FIG. 2B illustrates time change in X-ray energy in one shot of the X-rays from an X-ray irradiation unit with which a subject is irradiated and the number of shots of X-ray image data to be captured by one shot of the X-rays.

FIG. 2E illustrate time change in X-ray energy in one shot of the X-rays from an X-ray irradiation unit with which a subject is irradiated and the number of shots of X-ray image data to be captured by one shot of the X-rays.

FIG. 3A is a flowchart illustrating processing in the X-ray imaging apparatus according to the exemplary embodiment of the present invention.

FIG. 3C is a flowchart illustrating processing in the X-ray imaging apparatus according to the exemplary embodiment of the present invention.

DESCRIPTION OF EMBODIMENTS

Various exemplary embodiments, features, and aspects of the invention will be described in detail below with reference to the drawings.

In the following descriptions of exemplary embodiments of the present invention, it is described a case an X-ray imaging apparatus that performs imaging of X-ray image data of a subject using the X-ray that is a kind of radiation is applied as a radiation imaging apparatus according to the exemplary embodiments of the present invention. The exemplary embodiment of the present invention is not limited to the X-ray imaging apparatus. For example, the exemplary embodiment of the present invention can be applied to a radiation imaging apparatus that performs imaging of a radiation image of a subject using the other radiation such as alpha rays, beta rays, or gamma rays.

Figure 1:
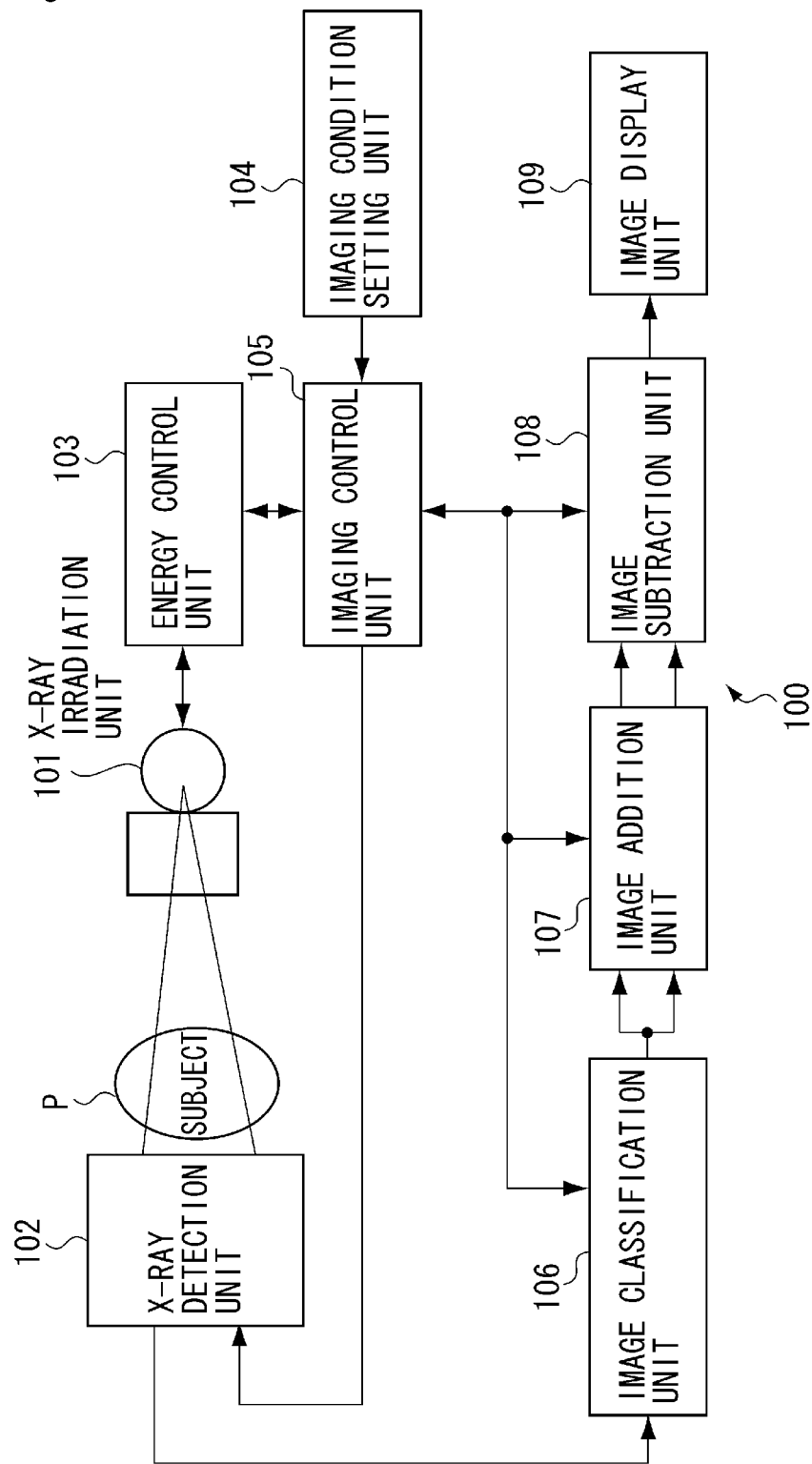
FIG. 1 illustrates a configuration of an X-ray imaging apparatus according to an exemplary embodiment of the present invention.

A first exemplary embodiment of the present invention is described. FIG. 1 illustrates an overall configuration of an X-ray imaging apparatus 100 according to the first exemplary embodiment of the present invention. The X-ray imaging apparatus 100 is specially used for medical purposes.

In FIG. 1, an X-ray irradiation unit 101 irradiates a subject P with X-rays. An X-ray detection unit 102 detects X-rays that transmitted through the subject P, and generates X-ray image data. The X-ray irradiation unit 101 includes an X-ray generation unit (tube) (not shown) that generates X-rays, and a collimator that defines a beam spreading angle of the X-rays generated in the X-ray generation unit. The X-ray detection unit 102 is formed by arranging fine solid-state image sensors two-dimensionally in grid-like manner.

An energy control unit 103 controls energy of the X-rays emitted from the X-ray irradiation unit 101. The energy control unit 103 can continuously adjust the energy of the X-rays in one shot that is emitted from the X-ray irradiation unit 101. An imaging condition setting unit 104 sets imaging conditions such as energy, a frame rate, and binning of the X-rays with which the subject is irradiated in response to an operation by an operator.

An image classification unit 106 classifies a plurality of sheets of the X-ray image data captured by the X-ray detection unit 102 into an X-ray image data group that is captured with high-energy X-ray beams and an X-ray image data group that is captured with low-energy X-ray beams.

An image addition unit 107 performs weighting on each X-ray image data included in the same group to each of the X-ray image data group that is captured with the high-energy X-ray beams and the X-ray image data group that is captured with the low-energy X-ray beams classified by the image classification unit 106. The image addition unit 107 performs addition to the weighted X-ray image data in the same group.

An image subtraction unit 108 performs weighting on the X-ray image data that is captured with the high-energy X-ray beams and the X-ray image data that is captured with the low-energy X-ray beams that are added by the image addition unit 107 respectively, and performs subtraction on the data. An image display unit 109 outputs the X-ray image data subtracted by the image subtraction unit 108 to a monitor or the like.

The X-ray irradiation unit 101 is an example of an irradiation unit according to the present invention. The energy control unit 103 is an example of a control unit according to the present invention. The X-ray detection unit 102 is an example of a generation unit according to the present invention. The image classification unit 106 is an example of a classification unit according to the present invention. The image subtraction unit 108 is an example of a subtraction unit according to the present invention. The image addition unit 107 is an example of an addition unit according to the present invention.

Next, with reference to FIG. 2A, time change in the X-ray energy in one shot of the X-rays from the X-ray irradiation unit 101 with which the subject P is irradiated and the number of shots of the X-ray image data to be captured by one shot of the X-rays. FIG. 2A illustrates a case in which imaging for separating soft tissue and bone portions is performed in chest radiography. In FIG. 2A, a tube voltage of an X-ray tube in one shot of the X-ray is continuously controlled. Further, in FIG. 2A, phases of a shot of the X-ray image data by the X-ray detection unit 102 and change in the tube voltage are shifted by an imaging control unit 105 between a case in which the tube voltage increases as time advances and a case in which the tube voltage decreases as time advances.

Furthermore, in FIG. 2A, high frame rate imaging is performed by performing 4*4 binning. Accordingly, in FIG. 2A, X-ray image data of the subject irradiated with different X-ray energy including 20 sheets of the X-ray image data captured with the high-energy X-ray beams and 20 sheets of the X-ray image data captured with the low-energy X-ray beams can be obtained in irradiation time of 100 ms of one shot of the X-rays. The binning is a method for reading a predetermined number of pixels (in the above exemplary example, 4*4) for detecting radiation as one unit.

With reference to a flowchart in FIG. 3A, the flow of the X-ray imaging processing in the X-ray imaging apparatus 100 is described. In FIG. 3A, a variable fmax is the number of shots of the X-ray image data (the number of X-ray image shots) set by an operator. A variable Vth is a threshold value of the tube voltage for distinguishing between the X-ray image data captured with the high-energy X-ray beams and the X-ray image data captured with the low-energy X-ray beams. A variable f is the number of shots of X-ray image data from the start of imaging. A variable Vf is a tube voltage applied to the tube in shooting of X-ray image data at the variable f.

In FIG. 3A, in step S101, the imaging condition setting unit 104 sets imaging conditions for shooting an image of a subject in response to an operation of the operator. The imaging conditions may include the number of shots of the X-ray image fmax, high and low tube voltages that are determined to be appropriate, the threshold value Vth of the tube voltage for distinguishing between the X-ray image data captured with the high-energy X-ray beams and the X-ray image data captured with the low-energy X-ray beams, and the like.

Then, in step S102, the imaging control unit 105 determines a tube voltage waveform for one shot of the X-ray as shown in FIG. 2A such that many shots of the X-ray image data at small tube voltage differences can be obtained around the tube voltage that is inputted by the operator and considered to be appropriate. Then, the imaging control unit 105 transmits a tube voltage control signal of the tube voltage waveform to the energy control unit 103.

In step S103, the imaging control unit 105 sets the variable f to an initial value zero. In step S104, the energy control unit 103 starts irradiation of the X-ray to the subject according to the tube voltage control signal in step S102.

In step S105, the imaging control unit 105 records the tube voltage waveform as Vf at the variable f determined in step S102. In step S106, the X-ray detection unit 102 detects the X-rays transmitted through the subject, and the detection result is stored as X-ray image data Rf. In step S107, the imaging control unit 105 adds one to the variable f to update the number of the X-ray image data pieces captured up until then.

In step S108, the imaging control unit 105 determines whether the value of the variable f is smaller than the value of the variable fmax to determine whether the number of the captured X-ray image data pieces captured up until then reaches the number of X-ray image shots set by the operator.

If the number of the X-ray image data pieces captured up until then reaches the number of X-ray image shots set by the operator (NO in step S108), the processing proceeds to step S109. Or if the number of the X-ray image data pieces captured up until then has not reached yet the number of X-ray image shots (YES in step S108), the processing returns to step S105. In step S109, the energy control unit 103 stops the X-ray irradiation to the subject by the X-ray irradiation unit 101.

The shooting of the first shot of the X-ray image data in step S106 is performed at the same time or before the X-ray irradiation in step S104 is performed. The shooting of the last shot of the X-ray image data in step S106 is performed until the X-ray irradiation in step S109 is completed.

In step S110, the image classification unit 106 classifies the X-ray image data pieces captured in step S106 into a group of the X-ray image data captured with the high-energy X-ray beams and a group of the X-ray image data captured with the low-energy X-ray beams.

In step S111, the image addition unit 107 performs addition of the X-ray image data by weighting to each X-ray image data in the group with respect to the X-ray image data pieces classified into the same group in step S110.

In step S112, the image subtraction unit 108 performs subtraction of the X-ray image data by weighting to both of the X-ray image data captured with the high-energy X-ray beams and the X-ray image data captured with the low-energy X-ray beams added in step S111. Processing performed in steps S110, S111, and S112 is described below in detail.

In step S113, the image display unit 109 displays the X-ray image data subtracted in step S112 on a monitor, or the like. The operator can check the X-ray image data displayed in step S113, and determine whether appropriate X-ray image data is obtained. If the operator determines that the appropriate X-ray image data is obtained, the operator performs an end operation. If the operator determines that the appropriate X-ray image data is not obtained, the operator performs an operation to change the weighting coefficient.

In step S114, the imaging control unit 105 determines whether the operation to change the weighting coefficient is performed. If the operation to change the weighting coefficient is performed (YES in step S114), the processing returns to step S111. Or if not the operation to change the weighting coefficient, but the end operation is performed (NO in step S114), the processing ends. The above-described steps 111 to 115 will be repeated until the operator determines the appropriate X-ray image data is obtained. By the above-described operation, the appropriate energy subtraction image data can be obtained.

Next, the flows of the image classification, the image addition, and the image subtraction are described with reference to the flowchart in FIG. 3B.

Figure 3B:
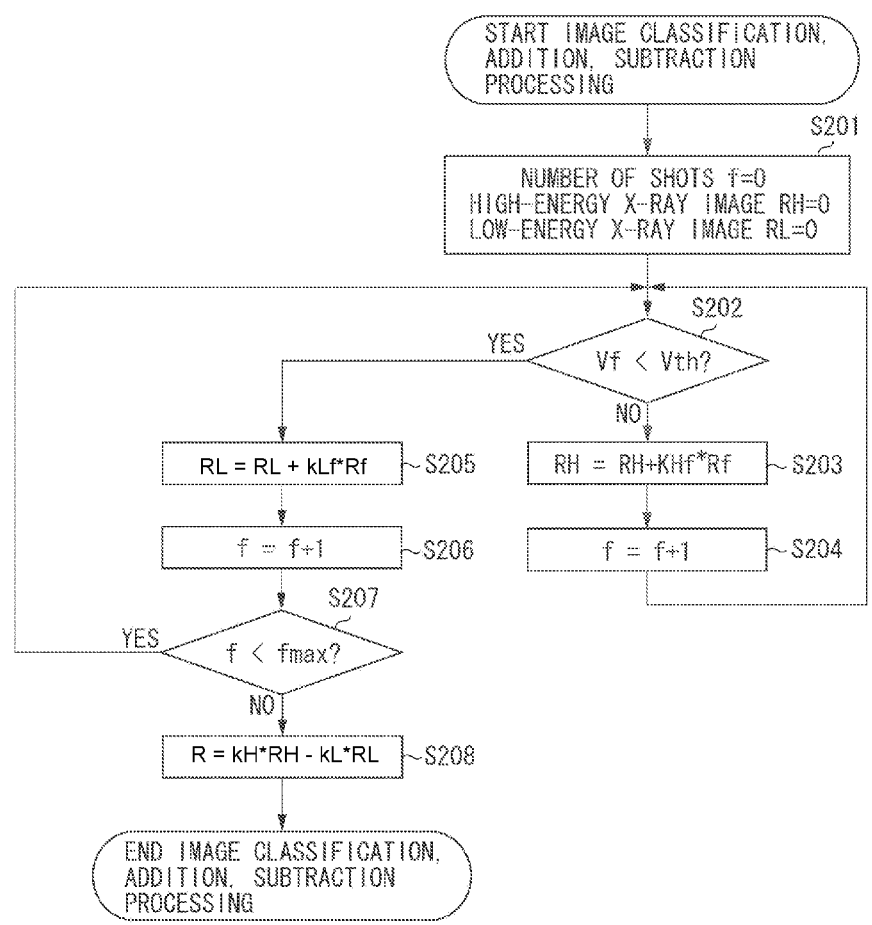
FIG. 3B is a flowchart illustrating processing in the X-ray imaging apparatus according to the exemplary embodiment of the present invention.

In FIG. 3B, a variable RH is the X-ray image data captured with the high-energy X-ray beams. A variable RL is the X-ray image data captured with the low-energy X-ray beams. A variable R is the X-ray image data obtained by performing the weighting and the subtraction to the X-ray image data pieces. Variables kHf and kLf are weighting coefficients for the respective X-ray image data pieces used in the addition of the X-ray image data captured with the high-energy X-ray beams and the X-ray image data captured with the low-energy X-ray beams. Variables kH and kL are weighting coefficients for the respective X-ray image data pieces used in the subtraction of the X-ray image data RH and the X-ray image data RL.

In step S201, the imaging control unit 105 returns the variable f to zero. Further, the imaging control unit 105 substitutes the initial value zero for all pixel values of the X-ray image data RH captured with the high-energy X-ray beams and the X-ray image data RL captured with the low-energy X-ray beams.

In step S202, the imaging control unit 105 determines whether the value of the variable Vf is smaller than the value of the variable Vth. In other words, the imaging control unit 105 determines whether the tube voltage Vf at the time of shooting the X-ray image data Rf is lower than the threshold value Vth. If the tube voltage Vf at the time of shooting the X-ray image data Rf is lower than the threshold value Vth (YES in step S202), the processing proceeds to step S205. On the other hand, if the tube voltage Vf at the time of shooting the X-ray image data Rf is equal to or greater than the threshold value Vth (NO in step S202), the processing proceeds to step S203.

In step S203, the imaging control unit 105 multiplies the X-ray image data Rf by the weighting coefficient kHf, and adds the weighted value to the X-ray image data RH. Thus, the X-ray image data captured with the high-energy X-ray beams is added. In step S204, the imaging control unit 105 adds one to the variable f to update the captured image that is the target of the addition.

In step S205, the imaging control unit 105 multiplies the X-ray image data Rf by the weighting coefficient kLf, and adds the weighted value to the X-ray image data RL. Thus, the X-ray image data captured with the low-energy X-ray beams is added. In step S206, the imaging control unit 105 adds one to the variable f to update the captured image that is the target of the addition. In step S207, the imaging control unit 105 determines whether the value of the variable f is smaller than the value of the number of X-ray image shots fmax. If the value of the variable f is smaller than the value of the number of X-ray image shots fmax (YES in step S207), the processing returns to step S202. Then, the processing from step S202 to step S206 is repeated until the last shot.

If the value of the variable f is equal to the value of the number of X-ray image shots fmax (NO in step S207), the processing proceeds to step S208. In step S208, the imaging control unit 105 multiplies the X-ray image data RH and the X-ray image data RL by the variables kH and kL respectively, and subtracts the both values. By the operation, difference image data between the X-ray image data captured with the high-energy X-ray beams and the X-ray image data captured with the low-energy X-ray beams can be obtained.

In the processing of the image classification, the image addition, and the image subtraction, initial values of the weighting coefficients kHf, kLf, kH, and kL of the X-ray image data can be any value. Further, as the initial values of the weighting coefficients kHf, kLf, kH, and kL, a plurality of combinations of these values can be made. Using each of the combinations, the processing from step S201 to step S208 can be performed, and a plurality of pieces of difference image data of different weighting coefficients can be generated. Then, these data pieces can be displayed on the display, and the operator can select an optimum image.

By the above-described processing, 20 sheets each of the X-ray image data of different irradiation X-ray energy groups, namely the high-energy side and the low-energy side, can be obtained at one shot of X-ray irradiation. Moreover, the operator can freely select the weighting coefficients in the addition of the X-ray image data at the high-energy side and the X-ray image data at the low-energy side respectively and the weighting coefficients in the subtraction of the X-ray image data at the high-energy side and the X-ray image data at the low-energy side. By this operation, the appropriate energy subtraction image data can be surely obtained in a single shooting.

A second exemplary embodiment of the present invention is described. An X-ray imaging apparatus according to the present exemplary embodiment has a configuration similar to that in the first exemplary embodiment shown in FIG. 1. However, functions of the imaging control unit 105 are different therefrom as described below.

In the first exemplary embodiment, the description is based on the assumption that the imaging region is the chest and the imaging is performed without using a contrast agent. Further, an age of a subject is not considered, and the binning in the single shooting is fixed. Moreover, the operator adjusts the parameters for performing the weighting of the X-ray image data to obtain appropriate energy subtraction image data.

In the second exemplary embodiment, it is possible to perform switching of the imaging region, imaging using a contrast agent, imaging by considering the age of the subject, and imaging by changing the binning in the single shooting. Further, an automatic adjustment function of the weighting coefficient for obtaining appropriate X-ray image data is provided.

For these purposes, the imaging control unit 105 according to the second exemplary embodiment includes a function for partially reading the X-ray image data, a region recognition function for recognizing a region based on the X-ray image data, and an interest region recognition function for recognizing an interest region of the X-ray image data and peripheral regions of the interest region based on a result of the region recognition by the region recognition function and imaging conditions set by the operator.

Figure 4:
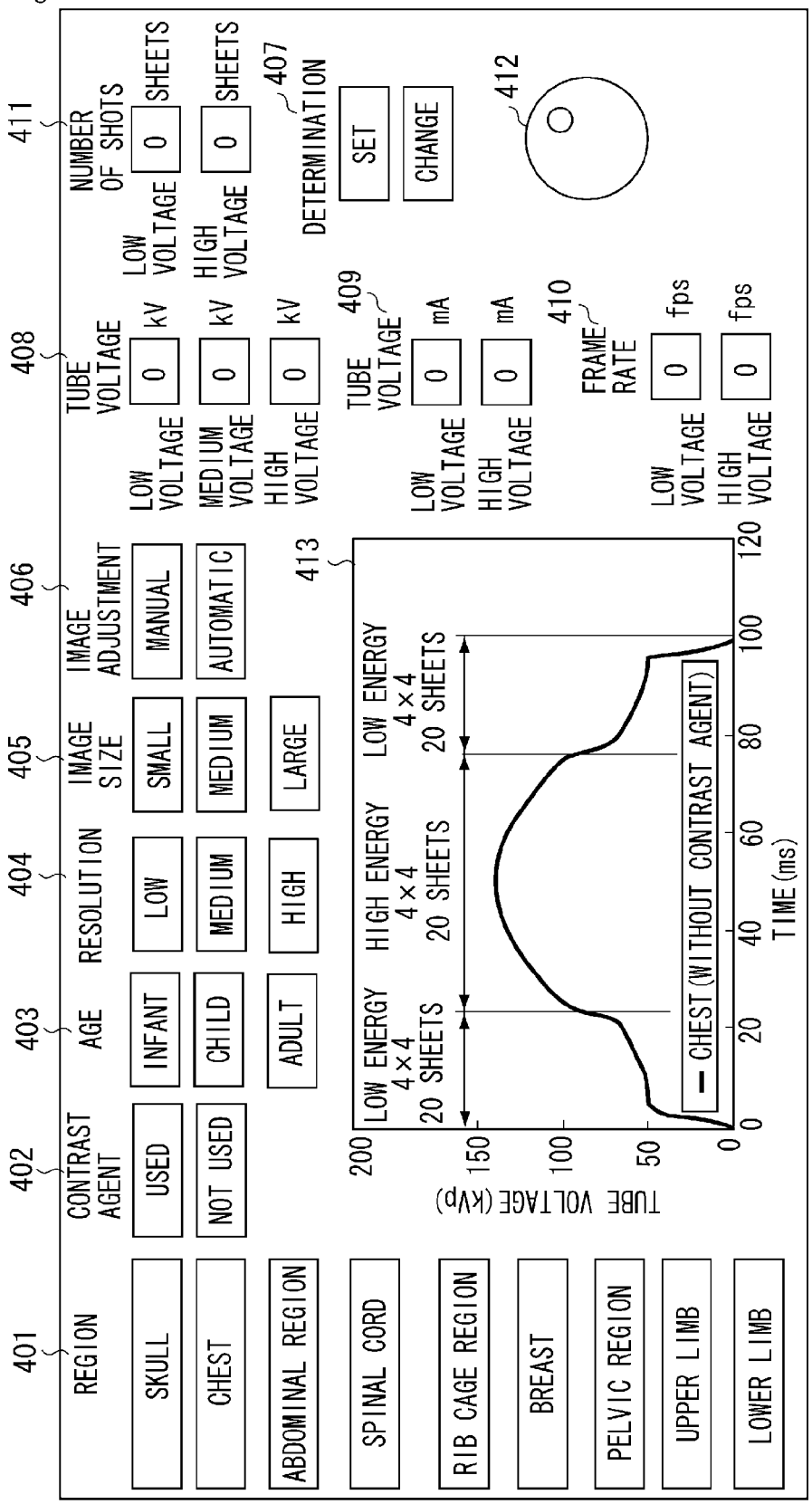
FIG. 4 illustrates a button layout on an operation screen displayed by a function of an imaging condition setting unit.

With reference to FIG. 4, the imaging condition setting unit 104 according to the second exemplary embodiment is described. FIG. 4 illustrates an example of a button layout on an operation screen displayed by the functions of the imaging condition setting unit 104 according to the second exemplary embodiment. The operation screen displayed by the imaging condition setting unit 104 includes selection buttons 401 to 407 for selecting a region, a contrast agent, an age, a resolution, an image size, image adjustment, and determination. Moreover, the operation screen includes adjustment windows 408 to 411 for tube voltage, tube current, a frame rate, and the number of shots, an adjustment dial 412, and a tube voltage waveform display window 413.

In the second exemplary embodiment, an operator inputs imaging conditions in the order of the region, the contrast agent, the age, the resolution, and the image size on the operation screen shown in FIG. 4. Then, at each step, a time change waveform of the tube voltage, binning, and the number of shots are displayed on the tube voltage waveform display window. Via each selection button and the adjustment window, the imaging conditions can be manually adjusted at each step. When the SET button is pressed, the conditions are inputted into the imaging control unit 105, and imaging can be performed under the conditions. Even after the SET button is pressed, the imaging conditions can be set again by pressing the CHANGE button.

Figure 2C:
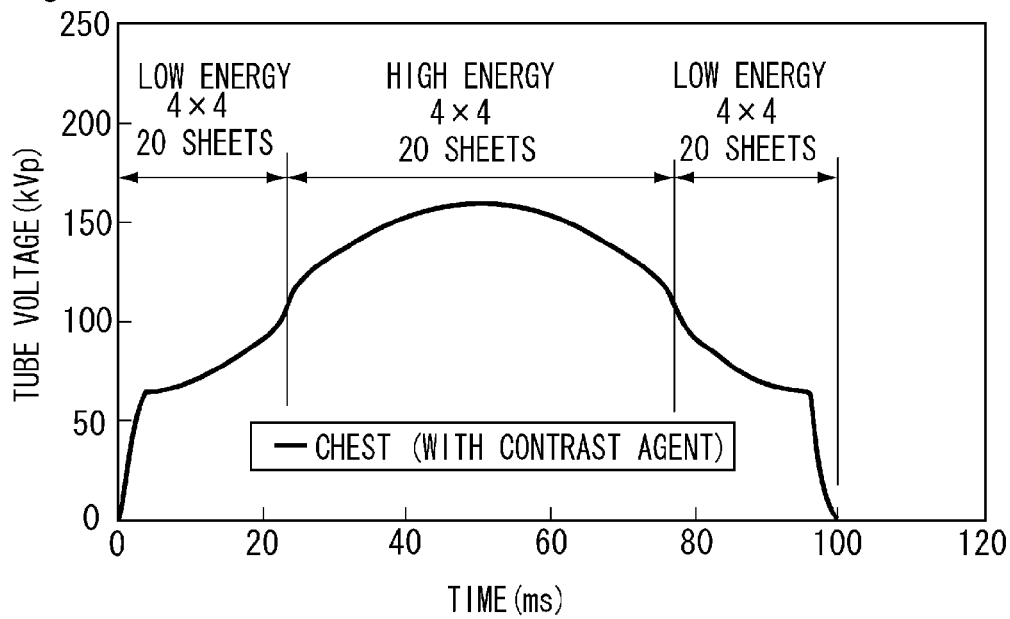
FIG. 2C illustrates time change in X-ray energy in one shot of the X-rays from an X-ray irradiation unit with which a subject is irradiated and the number of shots of X-ray image data to be captured by one shot of the X-rays.

Next, with reference to FIGS. 2B to 2E, imaging conditions automatically set as initial values when each selection button on the operation screen shown in FIG. 4 are described. FIG. 2B shows imaging conditions set to the imaging control unit 105 as initial values when a breast is selected as the region in FIG. 4.

The tube voltage in FIG. 2B is set to a value lower than that of the case for the imaging of the chest is FIG. 2A in order to erase mammary glands and to improve visualization of a tumor mass. Further, high-resolution imaging without binning is performed. As described above, in the second exemplary embodiment, the tube voltage and the binning can be changed depending on the imaging region.

FIG. 2C shows imaging conditions set to the imaging control unit 105 as initial values when a chest is selected as the region and use of a contrast agent is selected on the operation screen shown in FIG. 4. In FIG. 2C, in order to separate the contrast agent and bone portions, the tube voltage is set to a higher value as compared to the case of not using the contrast agent in FIG. 2A. As described above, in the second exemplary embodiment, the tube voltage can be changed depending on the use or nonuse of the contrast agent.

Figure 2D:
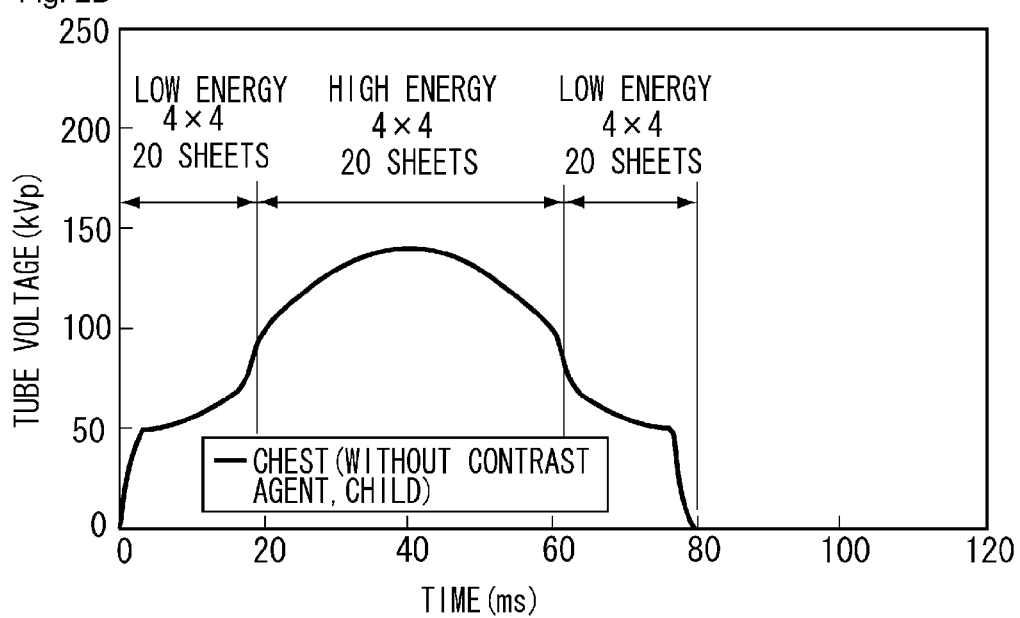
FIG. 2D illustrates time change in X-ray energy in one shot of the X-rays from an X-ray irradiation unit with which a subject is irradiated and the number of shots of X-ray image data to be captured by one shot of the X-rays.

FIG. 2D shows imaging conditions set to the imaging control unit 105 as initial values when a chest is selected as the region, nonuse of the contrast agent is selected, and child is selected as the age on the operation screen shown in FIG. 4. In FIG. 2D, since child's heartbeat is normally faster than that of adults and imaging in shorter time is required, the tube voltage is controlled such that the imaging time is shorter than that in the case of the adult shown in FIG. 2A. Moreover, in FIG. 2D, the imaging control unit 105 performs partial reading of the image to increase the frame rate that can be captured, and performs the imaging such that the energy resolution is not decreased as compared to the case in FIG. 2A. In the imaging of the child, the resolution can be decreased by binning as compared to the imaging of the adult, and the frame rate can be increased instead.

As described above, in the second exemplary embodiment, the partial reading of the X-ray image data, or the imaging with increased frame rate by binning can be performed depending on the age of the subject. The above-described processing of increasing the frame rate of the image data that is partially read as compared to the rate before the partial reading is performed, and the processing of increasing the frame rate after the resolution is decreased as compared to the rate before the resolution is decreased by binning are examples of processing of s changing unit according to the present invention.

FIG. 2E shows imaging conditions set to the imaging control unit 105 as initial values when a chest is selected as the region, nonuse of the contrast agent is selected, adult is selected as the age, and high is selected as the resolution on the operation screen shown in FIG. 4.

In FIG. 2E, the X-ray image data captured with the low-energy X-ray beams is generally hard to see the fine structure and deterioration in the image quality due to binning is small. Accordingly, imaging of the X-ray image data captured with the high-energy X-ray beams is performed by binning of 1*1, and imaging of the X-ray image data captured with the low-energy X-ray beams is performed by binning of 4*4. By changing the resolution by binning in the irradiation of the X-ray one shot, the imaging time can be shortened as compared to the imaging of binning of 1*1 with the high energy or the low energy, and a motion artifact can be reduced. As described above, in the second exemplary embodiment, binning can be changed in the single shooting.

A difference in shooting processing between the first exemplary embodiment and the second exemplary embodiment is described. The difference in the shooting processing between the first exemplary embodiment and the second exemplary embodiment is in the imaging condition setting processing in step S101 in the case that the image adjustment is manually set on the operation screen shown in FIG. 4. In the case that the image adjustment is automatically set, the imaging condition setting processing in step S101, the processing of determining the change in the weighting of the X-ray image data in step S114, and the weighting processing in step S115 are different.

Hereinafter, image optimization processing which is alternative processing in steps S114 and 115 when the image adjustment is automatically performed is described with reference to FIG. 3C. The processing of setting the image conditions in step S101 is performed as described above.

In step S301, the imaging control unit 105 performs region recognition by the region recognition function based on the first X-ray image data in step S112, and determines to which region the region of the X-ray image data corresponds. The method of the region recognition can be any method available to the public.

In step S302, the imaging control unit 105 sets an interest region and a peripheral region of the interest region by the interest region recognition function based on the result of the region recognition in step S301 and the imaging conditions set in step S101. The interest region and the peripheral region are, for example, in imaging with the contrast agent, the region of the contrast agent is the interest region and the region around the contrast agent is the peripheral region. The regions are set for each image condition in advance. The interest region and the peripheral region can be selected by the operator from the captured X-ray image data displayed on the monitor or the like. In step S302, the imaging control unit 105 defines a pixel value in the peripheral region as C, and a pixel value in the interest region as D.

In step S303, the imaging control unit 105 calculates the pixel value D in the interest region and the pixel value C in the peripheral region defined in step S302, and adjusts the variables kHf, kLf, kH, and kL such that contrast between these regions becomes maximum. The contrast is defined by the equation $E=|C-D|/C$.

The adjustment method of the variables kHf, kLf, kH, and kL can be any optimization method available to the public. For example, a genetic algorithm can be applied in which maximization of the variable E is set as an objective function and the variables kHf, kLf, kH, and kL are used as design variables. By the processing, the image optimization processing ends, and the operator can check the optimized X-ray image data.

By the above-described processing, as compared to the first exemplary embodiment, more appropriate energy subtraction image data can be obtained with fewer man-hours for the operator.

The exemplary embodiments of the present invention can be implemented by executing the following processing. That is, software (a program) to implement the functions of the above-described exemplary embodiments is supplied to a system or an apparatus via a network or various storage medium. A computer (or central processing unit (CPU) or micro processing unit (MPU)) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-015855 filed Jan. 27, 2010, which is hereby incorporated by reference herein in its entirety.

The invention claimed is:

1. A radiation imaging apparatus comprising:
an irradiation unit configured to irradiate a subject with radiations;
a control unit configured to continuously adjust energy of the radiations in one shot emitted by the irradiation unit;
a generation unit configured to generate a plurality of image data pieces in one shot by detecting the radiations whose energy is continuously adjusted by the control unit and transmitted through the subject;
a classification unit configured to classify the plurality of image data pieces generated by the generation unit into image data generated by the radiations of a high energy side and image data generated by the radiations of a low energy side;
a subtraction unit configured to perform weighting and subtraction on the image data generated by the radiations of the high energy side and the image data generated by the radiations of the low energy side; and
a changing unit configured to change a frame rate of the image data generated by the generation unit,
wherein the changing unit changes the frame rate based on at least one of an imaging region of the subject and an age of the subject.

2. The radiation imaging apparatus according to claim 1, further comprising a partial reading unit configured to perform partial reading of the image data generated by the generation unit,
wherein the changing unit sets the frame rate of the partially read image data higher than the frame rate of the image data before the partial reading is performed.

3. The radiation imaging apparatus according to claim 1, further comprising a binning unit configured to unite a predetermined number of pixels for detecting radiations included in the generation unit and read the image data,
wherein the changing unit sets the frame rate of the image data whose resolution is decreased by the binning unit higher than the frame rate of the image data before whose resolution is decreased by the binning unit.

4. A radiation imaging apparatus comprising:
an irradiation unit configured to irradiate a subject with radiations;
a control unit configured to continuously adjust energy of the radiations in one shot emitted by the irradiation unit;
a generation unit configured to generate a plurality of image data pieces in one shot by detecting the radiations whose energy is continuously adjusted by the control unit and transmitted through the subject;
a classification unit configured to classify the plurality of image data pieces generated by the generation unit into image data generated by the radiations of a high energy side and image data generated by the radiations of a low energy side;
a subtraction unit configured to perform weighting and subtraction on the image data generated by the radiations of the high energy side and the image data generated by the radiations of the low energy side; and
a binning unit configured to unite a predetermined number of pixels for detecting radiations included in the generation unit and read the image data,
wherein the binning unit changes the number of pixels for uniting and reading the image data while one shot of the radiations is emitted from the irradiation unit.

5. The radiation imaging apparatus according to claim 4, wherein the binning unit changes the number of pixels for uniting and reading the image data depending on a case in which the image data is generated with the radiations of the high energy side and a case in which the image data is generated with the radiations of the low energy side.

6. A radiation imaging apparatus comprising:
an irradiation unit configured to irradiate a subject with radiations;
a control unit configured to continuously adjust energy of the radiations in one shot emitted by the irradiation unit;
a generation unit configured to generate a plurality of image data pieces in one shot by detecting the radiations whose energy is continuously adjusted by the control unit and transmitted through the subject;
a classification unit configured to classify the plurality of image data pieces generated by the generation unit into image data generated by the radiations of a high energy side and image data generated by the radiations of a low energy side;
a subtraction unit configured to perform weighting and subtraction on the image data generated by the radiations of the high energy side and the image data generated by the radiations of the low energy side; and
a changing unit configured to change a frame rate of the image data generated by the generation unit,
wherein the changing unit changes the frame rate of the image data generated by the generation unit while one shot of the radiations is emitted from the irradiation unit.

7. The radiation imaging apparatus according to claim 6, wherein the changing unit changes the frame rate of the image data generated by the generation unit depending on a case in which the image data is generated with the radiations of the high energy side and a case in which the image data is generated with the radiations of the low energy side.

8. A radiation imaging method comprising:
irradiating a subject with radiations;
continuously adjusting energy of the radiations in one shot emitted by an irradiation unit;
generating a plurality of image data pieces in one shot by detecting the radiations whose energy is continuously adjusted by a control unit and transmitted through the subject;
performing partial reading of the image data generated in the generating;
classifying the plurality of image data pieces generated in the generating into image data generated by the radiations of a high energy side and image data generated by the radiations of a low energy side;
performing weighting and subtraction on the image data generated by the radiations of the high energy side and the image data generated by the radiations of the low energy side; and
changing a frame rate of the image data generated by the generation unit,
wherein, in the changing, changing the frame rate based on at least one of an imaging region of the subject and an age of the subject, and
wherein, in the changing, the frame rate of the partially read image data is set higher than the frame rate of the image data before the partial reading is performed.

9. A radiation imaging method comprising:
irradiating a subject with radiations;
continuously adjusting energy of the radiations in one shot emitted by an irradiation unit;
generating a plurality of image data pieces in one shot by detecting the radiations whose energy is continuously adjusted by a control unit and transmitted through the subject;
uniting a predetermined number of pixels for detecting the radiations and reading the image data;
classifying the plurality of image data pieces generated in the generating into image data generated by the radiations of a high energy side and image data generated by the radiations of a low energy side;
performing weighting and subtraction on the image data generated by the radiations of the high energy side and the image data generated by the radiations of the low energy side; and
changing a frame rate of the image data generated by a generation unit,
wherein, in the changing, changing the frame rate based on at least one of an imaging region of the subject and an age of the subject, and
wherein, in the changing, the frame rate of the image data whose resolution is decreased in the uniting is set higher than the frame rate of the image data before whose resolution is decreased in the uniting.

10. A radiation imaging method comprising:
irradiating a subject with radiations;
continuously adjusting energy of the radiations in one shot emitted by an irradiation unit;
generating a plurality of image data pieces in one shot by detecting the radiations whose energy is continuously adjusted by a control unit and transmitted through the subject;
uniting a predetermined number of pixels for detecting the radiations and reading the image data;
classifying the plurality of image data pieces generated in the generating into image data generated by the radiations of a high energy side and image data generated by the radiations of a low energy side;
performing weighting and subtraction on the image data generated by the radiations of the high energy side and the image data generated by the radiations of the low energy side; and
changing a frame rate of the image data generated by a generation unit,
wherein, in the changing, changing the frame rate based on at least one of an imaging region of the subject and an age of the subject,
wherein, in the uniting, the number of pixels for uniting and reading the image data is changed while one shot of the radiations is emitted in the irradiating, and
wherein, in the uniting, the number of pixels for uniting and reading the image data is changed depending on a case in which the image data is generated with the radiations of the high energy side and a case in which the image data is generated with the radiations of the low energy side.

11. A radiation imaging method comprising:
irradiating a subject with radiations;
continuously adjusting energy of the radiations in one shot emitted by an irradiation unit;
generating a plurality of image data pieces in one shot by detecting the radiations whose energy is continuously adjusted by a control unit and transmitted through the subject;
classifying the plurality of image data pieces generated in the generating into image data generated by the radiations of a high energy side and image data generated by the radiations of a low energy side;
performing weighting and subtraction on the image data generated by the radiations of the high energy side and the image data generated by the radiations of the low energy side; and
changing a frame rate of the image data generated by a generation unit,
wherein, in the changing, the frame rate of the image data generated in the generating is changed while one shot of the radiations is emitted in the irradiating, and
wherein, in the changing, the frame rate of the image data generated in the generating is changed depending on a case in which the image data is generated with the radiations of the high energy side and a case in which the image data is generated with the radiations of the low energy side.

12. An apparatus for radiation imaging using a radiation detector and a radiation source, the apparatus comprising:
an obtaining unit configured to obtain pieces of image data from the radiation detector, wherein the radiation detector has detected one shot of radiations emitted from the radiation source and transmitted through an object to generate the pieces of image data;
a classification unit configured to classify the obtained pieces of image data into a first group and a second group, wherein pieces of image data of the obtained pieces corresponding to a first energy range of the one shot of radiations are classified into the first group, and pieces of image data of the obtained pieces corresponding to a second energy range of the one shot of radiations are classified into the second group;
an addition unit configured to perform weighting and addition on pieces of image data of the first group corresponding to the first energy range and weighting and addition on pieces of image data of the second group corresponding to the second energy range classified by the classification unit; and
a subtraction unit configured to perform weighting and subtraction on the image data generated by the radiations of the first energy range and the image data generated by the radiations of the second energy range which are obtained by the addition unit.

13. The apparatus of claim 12, wherein
an imaging condition for the radiation detector is set in response to an operational input by a user.

14. The apparatus of claim 13, wherein
the imaging condition for the radiation detector includes a condition of binning for the radiation detector, a resolution of an image obtained from the radiation detector, a frame rate of the radiation imaging of the radiation imaging, a number of frames of the generated image.

15. The apparatus of claim 13, wherein
the operational input is corresponding to at least one of a body part of the object to be imaged, information concerning an age of the object, a condition during imaging of a contrast agent injected to the object, a condition of binning for the radiation detector, a resolution of an image obtained from the radiation detector, a size of an image obtained from the radiation detector, and a frame rate of the radiation imaging of the radiation imaging.

16. The apparatus of claim 12, further comprising:
a recognition unit configured to recognize an imaging region in an image obtained from the pieces of image data.

17. The apparatus of claim 12, further comprising:
a control unit configured to, according to an imaging region of the object, control an energy of the radiations emitted from the radiation source.

18. The apparatus of claim 12, further comprising:
a control unit configured to, according to whether or not a contrast agent is used for the radiation imaging, control an energy of the radiations emitted from the radiation source.

19. The apparatus of claim 12, further comprising:
a changing unit configured to, based on at least one of an imaging region of the object and an age of the object, change a frame rate of the radiation imaging.

20. The apparatus of claim 19, further comprising a partial reading unit configured to perform partial reading of the obtained pieces of image data,
wherein the changing unit is configured to set the frame rate of the partially read image data higher than the frame rate of the image data before the partial reading is performed.

21. The apparatus of claim 12, wherein the binning unit changes the number of pixels for uniting and reading the image data depending on a case in which the image data is generated with the radiations of the first energy range and a case in which the image data is generated with the radiations of the second energy range.

22. The apparatus of claim 12, wherein the subtraction unit performs the weighting such that a contrast of an interest region in the subtraction image is maximum.

23. The apparatus of claim 12, further comprising:
a control unit configured to continuously adjust energy of the radiations in the one shot emitted by the radiation source.

24. A radiation imaging apparatus comprising:
the apparatus of claim 12,
the radiation detector; and
the radiation source.

25. The apparatus of claim 12, further comprising:
a display control unit configured to display an imaging condition for radiation imaging.

26. The apparatus of claim 25, wherein
the display control unit is configured to display a graph which represents a temporal change of a tube voltage, of the one shot of radiations, applied to the radiation source.

27. The apparatus of claim 25, further comprising:
a setting unit configured to set an imaging condition, based on the set object information,
wherein the display control unit is configured to change the displayed graph, based on the set imaging condition.

28. The apparatus of claim 25, wherein
the display control unit is configured to display an imaging condition for the one shot of radiation, including at least one of a tube voltage applied to the radiation source, a tube current applied to the radiation source, an irradiation time span of the one shot of radiations, a frame rate of the radiation detector detecting the one shot of radiations, a number of frames of the pieces of image data while the one shot of radiations are emitted.

29. The apparatus of claim 25, wherein
the display control unit is configured to display at least one icon for setting an imaging condition including at least one of a tube voltage applied to the radiation source, a tube current applied to the radiation source, an irradiation time span of the one shot of radiations, a frame rate of the radiation detector detecting the one shot of radiations, and a number of frames of the pieces of image data while the one shot of radiations are emitted.

30. The apparatus of claim 25, wherein
the display control unit is configured to display at least one icon for setting an object information including at least one of a body part to be imaged, information indicating a contract dye is injected into the object during radiation imaging, and an age of the object.

31. The apparatus of claim 30, further comprising:
a setting unit configured to set an imaging condition, based on the set object information.

32. The apparatus of claim 25, wherein
the display control unit is configured to display at least one icon for setting an imaging condition including at least one of a resolution of one of the first and the second image, and a size of at least one of the first and the second image.

33. The apparatus of claim 30, further comprising:
a setting unit configured to set an imaging condition of the radiation detector, based on the set imaging condition.

34. A method for radiation imaging using a radiation detector and a radiation source, the apparatus comprising:
obtaining pieces of image data from the radiation detector, wherein the radiation detector has detected one shot of radiations emitted from the radiation source and transmitted through an object to generate the pieces of image data;
classifying the obtained pieces of image data into a first group and a second group, wherein pieces of image data of the obtained pieces corresponding to a first energy range of the one shot of radiations are classified into the first group, and pieces of image data of the obtained pieces corresponding to a second energy range of the one shot of radiations are classified into the second group;
performing weighting and addition on pieces of image data of the first group corresponding to the first energy range and weighting and addition on pieces of image data of the second group corresponding to the second energy range classified by the classifying; and
performing weighting and subtraction on the image data generated by the radiations of the first energy range and the image data generated by the radiations of the second energy range which are obtained by the performing weighting and addition.

35. A non-transitory computer-readable storage medium storing a program including instructions executed by a computer to perform the method of claim 34.

* * * * *